United States Patent [19]

Golik et al.

[11] Patent Number: 4,557,754
[45] Date of Patent: Dec. 10, 1985

[54] BIS-(N,N-DIMETHYL-N-CARBODECYLOX-YMETHYL-N-ETHYLENE-AMMONIUM)-SULPHIDE DICHLORIDE AND USE THEREOF

[75] Inventors: Georgy A. Golik; Yaroslav P. Demchenko; Miron O. Lozinsky; Vladlen V. Malovik; Valery Y. Semeny, all of Kiev, U.S.S.R.

[73] Assignee: Institut Organicheskoi Khimii, Kiev, U.S.S.R.

[21] Appl. No.: 177,538

[22] Filed: Aug. 13, 1980

[51] Int. Cl.⁴ .................... A01N 37/44; A01N 33/12; A61K 31/225; C07C 149/243

[52] U.S. Cl. .......................................... 71/98; 71/76; 514/547; 514/772; 514/835; 514/882; 514/886; 514/887; 514/900; 514/902; 514/925; 514/928; 514/938; 514/946; 514/958; 514/959; 514/970; 514/871; 560/153; 424/43; 424/DIG. 13

[58] Field of Search ............ 560/153; 71/98, 76; 424/168, 313, 54, 43, DIG. 13; 514/547, 835, 882, 887, 772, 900, 928, 938, 958, 959, 946

[56] References Cited

U.S. PATENT DOCUMENTS 3,444,222 5/1969 Roberts ........................... 560/153

OTHER PUBLICATIONS

Migrdichian, Org. Synthesis, vol. 1, (1957), pp. 476–477.

Weygand, Preparative Org. Chem., 1974, p. 460.

Primary Examiner—Vivian Garner
Attorney, Agent, or Firm—Ladas & Parry

[57] ABSTRACT

A novel compound bis-(N,N-dimethyl-N-carbodecyloxymethyl-N-ethyleneammonium)-sulphide dichloride of the formula

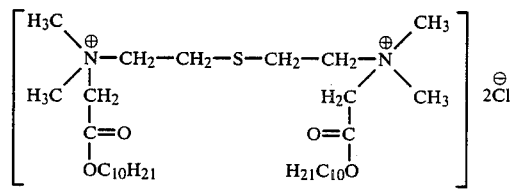

A method for preparing said novel compound comprising quaternization of bis-(β-dimethylaminoethyl)-sulphide with monochloroacetic acid decyl ester, molar ratio of said reagents being not more than 1:2.

A chemotherapeutic antimicrobial preparation comprising said novel compound as an active principle in combination with a pharmaceutical carrier.

A plant growth regulator in the form of an aqueous solution of said novel compound in a concentration of from 0.0001 to 0.1 wt. %.

9 Claims, No Drawings

BIS-(N,N-DIMETHYL-N-CARBODECYLOX-YMETHYL-N-ETHYLENE-AMMONIUM)-SULPHIDE DICHLORIDE AND USE THEREOF

The present invention relates to a novel substance which is a salt of quaternary ammonium bases, namely, to bis-(N,N-dimethyl-N-carbodecyloxymethyl-N-ethyleneammonium)-sulphide dichloride and to the use thereof.

According to the invention, bis-(N,N-dimethyl-N-carbodecyloxymethyl-N-ethyleneammonium)-sulphide dichloride has the following structural formula:

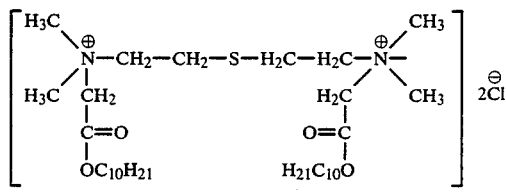

The above compound is a colourless crystalline substance soluble in water and lower alcohols and insoluble in diethyl ether. It crystallizes from acetone. The melting temperature is from 156° to 158° C. (with decomposition).

Bis-(N,N-dimethyl-N-carbodecyloxymethyl-N-ethyleneammonium)-sulphide dichloride is a pharmacologically active substance and may be successfully used in medicine and veterinary medicine for treating trophic ulcers, burns, and like damages of skin and mucous membranes, dermatoses, dermatomycoses, various inflammatory and respiratory diseases and gastro-intestinal disturbances.

Antimicrobial properties of said preparation were investigated by a classical method of series dilutions in standard liquid nutrient media.

The activity of the above preparation was tested by its action on staphylococci, *Escherichia coli*, and intestinal group microorganisms. Test results are given in Table 1.

TABLE 1

Antimicrobial activity of bis-(N,N—dimethyl-N—carbodecyloxymethyl-N—ethyleneammonium)-sulphide dichloride

| Item No. | Microorganisms | Number of strains | Average concentrations, μg/ml Bacteriostatic | Bactericidal |
|---|---|---|---|---|
| 1. | Staphylococcus aureus | 20 | 0.76 | 2.63 |
| 2. | Staphylococcus albus | 20 | 0.6 | 1.67 |
| 3. | Escherichia coli | 10 | 3.9 | 6.4 |
| 4. | Proteus morgani | 4 | 50.7 | 50.7 |
| 5. | Proteus vulgaris | 2 | 62.5 | 62.5 |
| 6. | Shigella sonnei | 7 | 5.85 | 28.4 |
| 7. | Salmonella sp. | 7 | 31.2 | 31.2 |

Bis-(N,N-dimethyl-N-carbodecyloxymethyl-N-ethyleneammonium)-sulphide dichloride was tested for toxicity in an acute test on rats of both sexes with an average mass of 200 to 250 g and on white mice of both sexes with an average mass of 22 to 25 g with enteral and intraperitoneal administrations. Aqueous solutions of the above preparation (from 10 to 5000 mg per kg of animal weight) were used for enteral and intraperitoneal administration. Each dosage was tried on five animals. Animal death rate was registered 24 hours after the administration of the above solutions.

Test results processed statistically by Rot modification of Litchfield and Wilcoxon method are given in Table 2.

TABLE 2

Toxicity of bis-(N,N—dimethyl—N—carbodecyloxymethyl-N—ethylene ammonium)-sulphide dichloride in acute test

| Animal species | Administration | $LD_{50}$ mg/kg | $LD_{100}$ mg/kg |
|---|---|---|---|
| 1 | 2 | 3 | 4 |
| Mice | Enteral | 1215 | 2500 |
|  | Intraperitoneal | 54.1 | 70.0 |
| Rats | Enteral | 2665 | 3500 |
|  | Intraperitoneal | 67.7 | 80.0 |

In studying the toxicity of bis-(N,N-dimethyl-N-carbodecyloxymethyl-N-ethylene ammonium)-sulphide dichloride in a chronic test the above preparation at a concentration of 0.2 wt.% in sodium chloride solution was administered intravenously to 35 to 40 kg calves daily for 30 days at a rate of 10 mg per kg of live weight. Test group consisted of 10 calves, the other 10 calves to which the above preparation was not prescribed making up a control group. The calves of both groups were kept in the same conditions. General state and behaviour of the calves, rate of gain were controlled and peripheric blood counts (hemoglobin, erythrocytes, leucocytes, thrombocytes, differential blood count) were made daily during the test. To determine the functional state of liver, kidneys, and pancreas, certain biochemical characteristics of the urine (protein, sugar, and biliary pigments content) and blood (sugar, cholesterol, bilirubin, urea, alkaline phosphatase, and chlorides content) were studied.

At the end of the test period the test group animals were killed and their internal organs were studied by macro- and microscopic techniques.

The observations showed that the above dosage of bis-(N,N-dimethyl-N-carbodecyloxymethyl-N-ethyleneammonium)-sulphide dichloride did not cause significant changes in the calves under the chronic test conditions. Test calves did not differ from the control ones in all the characteristics studied.

The autopsy and both macro- and microscopic study of brain, heart, liver, spleen, kidneys, adrenal glands, gastroenteric tract, ovary, bone marrow, pancreas, and goiter gland revealed no pathologic changes.

Aqueous solutions of the preparation were stable. The preparation did not lose its activity after being kept as 1% and 0.1% solutions for 6 months. Single and double autoclaving of the above compound for 60 minutes at 2.5 atm did not alter the antimicrobial activity thereof either.

The antimicrobial activity of the preparation remains unchanged at pH values from 5 to 8 which are characteristic for biological media.

The analysis of the test results suggests that bis-(N,N-dimethyl-N-carbodecyloxymethyl-N-ethyleneammonium)-sulphide dichloride displays strong antimicrobial action and belongs to the group of low-toxic substances.

According to the invention, the novel chemotherapeutic antimicrobial preparation comprises bis-(N,N-dimethyl-N-carbodecyloxymethyl-N-ethyleneammonium)-sulphide dichloride as its active principle in combination with a pharmaceutical carrier.

For lavages or lotions, enteral administration and dropwise administration into the otic cavity it is preferable to use as a pharmaceutical carrier sodium chloride solution with the active principle concentration of from 0.01 to 0.5 wt.%.

One of the versions of the chemotherapeutic antimicrobial preparation with the use of physiological solution as a pharmaceutical carrier, comprising the following ingredients:

| active principle | 0.1 g |
|---|---|
| sodium chloride | 5.9 g |
| distilled water | 1000 ml | was tested in stomatology for treating chronic apical pericementetis.

The preparation of the above composition was prepared as follows: the ingredients were measured in quantities equal to those indicated above or scaled up; distilled water was heated to a temperature of from 30° to 40° C.; the active principle was dissolved in the thus heated distilled water; sodium chloride was added to the solution obtained which was then stirred to complete dissolution of sodium chloride.

The treatment procedure was as follows.

Carious cavity was mechanically cleaned and shaped by conventional means, the contents of the root canals was evacuated with a pulp extractor under a hydrogen peroxide solution, the cleaned cavity was washed with water and with the chemotherapeutic antimicrobial preparation of the above-indicated composition. Then a tampon was soaked in a portion of the preparation, placed into the pulp cavity prepared as described above, and electrophoresis was performed for 20 to 30 min at 2.3 to 3.0 mA. The pulp cavity thus treated was dried in a conventional manner then stopped, starting from the root canals.

The above procedure was used for treating 775 teeth in 630 patients; 195 of them were observed for 2 years for individual results. Complications or disease recurrences were not observed.

Another version of the chemotherapeutic antimicrobial preparation with the use of a physiological solution as a pharmaceutical carrier, comprising the following ingredients:

| active principle | 1 g |
|---|---|
| sodium chloride | 9 g |
| distilled water | 1000 ml | was tested in treating gastroenteric tract diseases in younger farm animals (calves and sucking-pigs).

The preparation of the above-indicated composition was prepared as hereinbefore described. From 10 to 20 g of powdered glucose were added to the solution to improve the taste thereof.

Calves suffering from toxic dyspepsia, colibacteriosis, and salmonellosis, and sucking-pigs suffering from gastroenteritis of infectious ethnology underwent the treatment.

The treatment procedure was as follows. The preparation of the above composition was administered to sick animals per os at a rate of 10 mg per kg of live weight. If necessary, for example, when diarrhea in toxic dyspepsia continued, the administration of the same preparation dose was repeated in 24 to 28 hours. Sick calves were given the preparation through a nipple fountain and to sucking-pigs it was introduced into the mouth with the help of a syringe with a rubber tube.

Before giving the preparation, feeding the animals with beestings or milk was skipped and after the introduction (in 3 to 4 hours) beestings or milk were given in small portions.

The preparation has a high chemotherapeutic effect (see Table 3) which is especially important in cases of high animal concentration at large farms.

Treating animals with the preparation of the above composition makes it possible to exclude the application of antibiotics.

TABLE 3

Efficiency of treating younger farm animals with gastroenteric diseases

| Item No. | Disease | Number of sick animals | Results | | | |
|---|---|---|---|---|---|---|
| | | | Recovered | | Died | |
| | | | animals | % | animals | % |
| 1. | Toxic dyspepsia in calves | 190 | 177 | 93.2 | 13 | 6.8 |
| 2. | Colibacteriosis in calves | 86 | 78 | 90.7 | 8 | 9.8 |
| 3. | Salmonellosis in calves | 28 | 26 | 92.8 | 2 | 7.1 |
| 4. | Infectious gastroentherites in sucking-pigs | 1004 | 9906 | 98.6 | 14 | 1.4 |

A third version of the chemotherapeutic antimicrobial preparation with the use of physiological solution as a pharmaceutical carrier, comprising the following ingredients:

| active principle | 2 g |
|---|---|
| sodium chloride | 9 g |
| distilled water | 1000 ml | was tested in treating inflammatory diseases of the middle ear in men: acute otitis and antritis media purulenta, chronic purulent mesotympanitis, and chronic purulent epitympanitis.

The preparation of the above indicated composition was prepared as hereinbefore described.

The treatment was applied to 65 patients.

The treatment procedure consisted in thorough and copious irrigation (with the help of Hartmann's cannula or blunt-ended needle) of the middle ear, attic, and Eustachian tube for maximum removal of purulent exudate and cholesteatoma masses. If granulations were revealed in the middle ear during the preliminary examination, they were first removed therefrom.

Curing chronic purulent mesotympanitis (to dry otitis media) requires from 6 to 7 irrigations of tympanic cavity. Curing chronic purulent epitympanitis (to a dry state) requires, on an average, from 7 to 9 irrigations of the tympanic cavity and attic.

Recovery of all patients was achieved.

Remote results confirmed high therapeutic efficiency of the preparation as no exacerbations or complications were observed.

The use of solutions of penicillin, streptomycin, and other chemical preparations for the same purpose required twice as many or even more irrigations of the tympanic cavity and in a great number of cases did not result in recovery.

A fourth version of the chemotherapeutic antimicrobial preparation with the use of physiological solution as a pharmaceutical carrier, comprising the following ingredients:

| | |
|---|---|
| active principle | 5 g |
| sodium chloride | 9 g |
| distilled water | 1000 ml | was tested in treating chronic tonsillitis in children.

The preparation of the above-indicated composition was prepared as hereinbefore described.

The treatment was applied to 124 children aged from 5 to 12. In patients were observed hyperemia and vasodilatation of palatal arches, marked enlargement and friability of faucial tonsils, purulent plugs in lacunas, and enlargement of regional lymph nodules.

The treatment with the preparation of the above-indicated composition consisted in irrigating faucial tonsil lacunas once a day; the treatment course lasted, on an average, from 8 to 10 days. Each child was subjected to 1 or 2 courses.

In most of the patients (82) even 2 to 4 irrigations markedly improved general condition, reduced the effects of tonsilogenous intoxication, normalized the temperature, improved the appetite, reduced or completely removed hyperemia of tonsils and palatal arches and inflammation of throat mucous coat. In many patients a relatively rapid regression of cervical and submaxillary lymphadenites was noted.

Repeated examination of 108 children did not reveal exacerbation of chronic tonsillitis.

According to the invention, it is preferable that the composition of the chemotherapeutic antimicrobial preparation comprising bis-(N,N-dimethyl-N-carbodecyloxymethyl-N-ethyleneammonium)-sulphide dichloride as the active principle and physiological solution as the pharmaceutical carrier should also include glycerol in an amount of 2.5 to 3.0 wt.%. Glycerol stabilizes therapeutic aerosols prepared from the proposed chemotherapeutic antimicrobial preparation and aids to speed up the absorption of the above active principle through mucous coats of the oral cavity and respiratory organs.

One of the versions of such chemotherapeutic antimicrobial preparation modified with glycerol and comprising:

| | |
|---|---|
| active principle | 2 g |
| sodium chloride | 30 g |
| distilled water | 1000 ml | was tested for mass treatment and prophylaxis of respiratory diseases in younger farm animals.

The preparation of the above-indicated composition was prepared substantially as hereinbefore described. Glycerol was added after dissolving sodium chloride.

The treatment procedure consisted in the preparation of a fine dispersed aerosol containing 10 ml of the preparation of the above composition per $m^3$ of the air space within the building where sick animals were kept. To prepare the aerosol, a spray generator working at 4 to 5 atm of compressed air was used. Prior to mass inhalation treatment the building was made leak-proof. The duration of the inhalation treatment was 1 hour. After the treatment the building was ventilated. The treatment course consisted of 9 inhalation treatments at a rate of one treatment a day with 5- or 6-day intervals after the third and sixth days.

The application of the above treatment procedure in a calfpen of a cattle-breeding farm housing 2314 sick calves resulted in complete recovery of 2278 calves (98%).

To prevent acute respiratory diseases, it is recommendable to perform the above-described inhalation treatments 3 times in succession with a one day interval between the treatments and to repeat this triple inhalation in 8 or 10 days. This treatment reduces the sick rate to 2 to 3% of the live-stock.

Application of the preparation of the above composition in aerosol form ensures a high therapeutic and prophylactic effect (up to 98%). Aerosol does not have any adverse effect on calves and sucking-pigs and provides for a 5- to 8-fold decrease in bacterial contamination of air inside the buildings. Of additional interest is the fact that the personnel of cattle-breeding farms participating in the described treatment or prophylaxis of acute respiratory diseases in animals also acquires better resistance to these diseases.

According to the invention in the chemotherapeutic antimicrobial preparation intended for application or tamponing it is preferable to use as a pharmaceutical carrier an ointment base comprising from 0.1 to 2 wt.% of the active substance.

For treating men it is preferable to use the ointment base in the form of an emulsion "distilled water in lanoline", which emulsion comprises from 18.0 to 19.9 parts by weight of distilled water per 80 parts by weight of lanoline.

The following composition is an example of the chemotherapeutic antimicrobial preparation with the use of the above ointment base as the pharmaceutical carrier (all ingredients are in parts by weight):

| | |
|---|---|
| active principle | 0.1 |
| distilled water | 19.9 |
| anhydrous lanoline | 80.0. |

The ointment of the above composition was prepared as follows. The required ingredients were measured in accordance with the ratio indicated, an active substance, i.e. bis-(N,N-dimethyl-N-carbodecyloxymethyl-N-ethyleneammonium)-sulphide dichloride was dissolved in distilled water, and the resulting solution was mixed in a porcelain mortar with lanoline until a homogeneous emulsion was obtained.

The ointment thus prepared was tested in treating nipple cracks in puerperas. 210 puerperas aged from 17 to 39 were under observation. In 95 women the cracks of one nipple and in 115 women the cracks of both nipples were observed. 120 women had superficial cracks and 90 women had deep cracks. The ointment was applied on a tampon to the nipple crack immediately after breast feeding, and the tampon was fixed with an adhesive tape. Prior to next breast feeding, the ointment was removed and the nipple was successively treated with a 40% aqueous solution of ethyl alcohol, then with a furacin solution and washed with water. Breast feeding was not stopped during the treatment.

Due to the intimate contact of the ointment with the damaged surface many puerperas as soon as by the next day noted a considerable relief and decrease in painfulness during breast feeding. Nipple crack healing was achieved after 1 to 8 days. Treatment duration depended upon the depth of cracks.

No complication effects were observed after treatment with the ointment. The treatment did not disturb normal lactation. No changes in the oral cavity or intestine function of newborns were observed.

Another example of the chemotherapeutic antimicrobial preparation with the use of the above-described ointment base as the pharmaceutical carrier is an ointment of the following composition (in parts by weight):

| active principle | 1 |
|---|---|
| distilled water | 19 |
| anhydrous lanoline | 80 |

The ointment of the above composition was prepared as hereinbefore described.

This ointment was tested in treating acute and chronic inflammatory processes of female genital organs: inflammations of mucous coat of the vagina, inflammations of the tubes and ovary, uterus neck erosion. Treatment for these diseases was performed for 476 women of fertility age.

The treatment procedure consisted in inserting cottongauze tampons abundantly soaked in the above ointment into the vagina for 6 to 8 hours during 5 to 10 days in succession, the treatment course being controlled by vaginal smear analysis, visual observation of the quantity and appearance of vaginal discharge and by microbiological tests.

After three or four procedures all patients noted soothing of pain, reduction in the quantity of leucorrhea, and disappearance of pruritis. Vaginal smears became free of pathogenous microflora and the number of leucocytes therein progressively reduced.

Still another example of the chemotherapeutic antimicrobial preparation with the use of the above-described ointment base as the pharmaceutical carrier is an ointment of the following composition (in parts by weight):

| active principle | 2.0 |
|---|---|
| distilled water | 18.0 |
| anhydrous lanoline | 80.0 |

The ointment of the above composition was prepared as hereinbefore described.

This ointment was tested in treating 89 patients of both sexes and various age suffering from trophic ulcers of the crus with the disease duration from 2 to 2.5 years. The treatment procedure consisted in the following.

In cases with purulent discharge the treatment started with the application of a bandage soaked in a 1% aqueous solution of the active principle with 9% of sodium chloride. When the wound was free from purulent discharge, the treatment was continued by applying the ointment of the above composition until complete healing or appreciable improvement was achieved.

The treatment resulted in complete healing in 84% of the patients; the rest were released with a considerable improvement. The healing period depended on the size of the wound and ranged from 10 to 15 days for a 4 to 5 cm$^2$ wound area, from 18 to 30 days for a 10 to 20 cm$^2$ wound area, and from 50 to 55 days for a 35 to 40 cm$^2$ wound area.

Healing was observed also in patients suffering from chronic ulcerative pyoderma, piococcus ulcers, and crus ecthima.

No recurrences of the diseases were observed in cured patients.

For treating farm animals and superficial skin damage in men it is preferable to use the ointment base in the form of distilled water emulsion in lanoline—medicinal vaseline mixture. This emulsion comprises 40 parts by weight of lanoline, 50 parts by weight of medicinal vaseline, and from 8.0 to 9.9 parts by weight of water.

The following composition is an example of the chemotherapeutic antimicrobial preparation with the use of the above ointment base as the pharmaceutical carrier (all ingredients are in parts by weight):

| active principle | 0.1 |
|---|---|
| distilled water | 9.9 |
| anhydrous lanoline | 40.0 |
| medicinal vaseline | 50.0 |

The ointment of the above composition was prepared as follows. The required ingredients were measured in accordance with the ratio indicated; bis-(N,N-dimethyl-N-carbodecyloxymethyl-N-ethyleneammonium)-sulphide dichloride (the active principle) was dissolved in distilled water; lanoline was thoroughly mixed with medicinal vaseline in a porcelain mortar; the aqueous solution of the active principle was added to the resulting mixture and all the ingredients were thoroughly mixed until a homogeneous emulsion was obtained.

The ointment was used for treating nipple cracks in 140 cows during lactation.

The treatment procedure consisted in the following. After each milking the ointment was applied on a tampon to the nipple crack and the tampon was fixed with an adhesive tape. Immediately prior to next milking the tampon was removed and the nipple was successively washed with a 40% aqueous solution of ethyl alcohol and water and dried with a towel. After milking the ointment was applied again as described above. The procedure was repeated till complete healing of the crack.

Treatment duration varied from 2 to 10 days depending on the crack depth. Observations and analysis showed no effect of the above-described treatment on lactation or milk quality.

Another example of the chemotherapeutic antimicrobial preparation with the use of the above ointment base as the pharmaceutical carrier is an ointment of the following composition (in parts by weight):

| active principle | 1 |
|---|---|
| distilled water | 9 |
| anhydrous lanoline | 40 |
| medicinal vaseline | 50 |

The ointment of the above composition was prepared as hereinbefore described.

The ointment thus obtained was tested in treating inflammatory diseases of mucous coat of the vagina in 92 dry cows.

The treatment procedure consisted in introducing cotton-gauze tampons abundantly soaked in the above ointment into the vagina for 6 to 8 hours several days in succession till complete healing controlled visually and by microbiological tests was achieved.

In all cases complete healing was observed. All cured cows, on artificial insemination, gave birth to healthy calves.

Still another example of the chemotherapeutic antimicrobial preparation with the use of the above ointment base as the pharmaceutical carrier is an ointment of the following composition (in parts by weight):

| active principle | 2 |
| --- | --- |
| distilled water | 8 |
| anhydrous lanoline | 40 |
| medicinal vaseline | 50 |

The ointment of the above composition was prepared as hereinbefore described.

This ointment was tested in treating 82 children of both sexes aged from 5 to 12 and suffering from primary and secondary pyoderma complicated in some cases with cutaneous ulcers.

The treatment procedure consisted in applying the above ointment to damaged areas during 5 to 14 days, the bandage being changed every morning and evening.

Recovery was achieved in 74 patients. In remaining 8 children the treatment was suspended after 3 to 5 days for reasons irrelevant to the treatment course, and the control of the ointment action in these cases was therefore impossible.

For treating acute inflammatory diseases it is preferable to use the ointment base in the form of an emulsion "distilled water in polyvinyl butyl ether", said emulsion comprising from 9.0 to 9.9 parts by weight of water per 90 parts by weight of polyvinyl butylether.

One of the examples of the chemotherapeutic antimicrobial preparation with the use of the above ointment base is an ointment comprising (in parts by weight):

| active principle | 0.2 |
| --- | --- |
| distilled water | 9.8 |
| polyvinyl butyl ether | 90.0 |

Polyvinyl butyl ether known in pharmacology as "Shostakovsky's balsam" or "Vinylin" is a thick viscous light-yellow liquid with a specific odour, practically insoluble in water, miscible with chloroform, ether, vegetable oils and having a density from 0.903 to 0.921 g/cm$^3$.

The ointment of the above composition was prepared as follows. The required ingredients were measured in accordance with the ratio indicated; bis-(N,N-dimethyl-N-carbodecyloxymethyl-N-ethylenammonium)-sulphide dichloride (the active principle) was dissolved in water and the resulting solution was thoroughly mixed in a porcelain mortar with polyvinyl butyl ether until a creamy mass was obtained.

The ointment thus prepared was tested in treating 164 adult patients suffering from inflammatory diseases of the rectum and pararectal tissue, including 64 patients with cracks in the anal area, 44 patients with inflammation of hemorrhoids, 19 patients with the anal fistula, 18 patients with acute periproctitis, and 16 patients with proctitis and proctosigmoiditis.

The treatment with the ointment of the above composition consisted in the following. Prior to sleep the patients took a cleansing enema and washed up with warm water, dried the skin with a soft towel, and a turunda abundantly soaked in the ointment was introduced into the anus. If necessary, the area adjacent to the anus was additionally covered with a layer of the ointment. This procedure was repeated every evening for 7 to 12 days.

Generally, by the next day pain and pruritis reduced or disappeared altogether.

Both immediate and remote results followed for one year are good.

Another example of the chemotherapeutic antimicrobial preparation with the use of the ointment base containing polyvinyl butyl ether is an ointment comprising (in parts by weight):

| active principle | 0.5 |
| --- | --- |
| distilled water | 9.5 |
| polyvinyl butyl ether | 90.0 |

The ointment of the above composition was prepared as herinbefore described.

This ointment was tested in stomatological treatment of 289 patients, from 4.5 months to 55 years of age, including 139 patients suffering from acute aphtous stomatitis, 93 patients suffering from chronic recurrent stomatitis, and 66 patients suffering from ulcerative stomatitis.

The treatment procedure consisted in the following. After thorough toilet of the oral cavity (removal of dental calculus and gargle with 3% aqueous solution of hydrogen peroxide) a thin layer of the ointment was applied to the injured areas of the mucous coat for 15 to 20 min.

Painfulness of the mucous coat disappeared immediately after the first application. The next day the ulcers became free of coating, and a reduction of hyperemia, mucous coat edema around the ulcers, and salivation were noted. Ulcer healing without any scars was observed on the 3rd or 4th day.

In chronic recurrent stomatitis, the above treatment resulted in recurrence delay, which was not attainable with other methods of treatment.

According to the invention, it is preferable to use for stomatological practice a mixture of peach kernel oil and artificial dentin as a pharmaceutical carrier with the following ingredient ratio (in parts by weight):

| active principle | from 5 to 7 |
| --- | --- |
| peach kernel oil | from 20 to 24 |
| artificial dentin | from 70 to 73 |

One of the examples of the chemotherapeutic antimicrobial preparation intended for use in stomatology is a paste of the following composition (in parts by weight):

| active principle | 5 |
| --- | --- |
| peach kernel oil | 22 |
| artificial dentin | 73 |

The paste of the above composition was prepared ex tempera as follows. Bis-(N,N-dimethyl-N-carbodecyloxymethyl-N-ethyleneammonium)-sulphide dichloride (the active principle) was mixed on a glass with peach kernel oil, artificial dentin was added to the mixture obtained and all the ingredients were thoroughly mixed with a spatula until a doughlike paste was obtained.

The paste was tested in treating uncomplicated deep caries of 288 teeth in 146 patients.

The treatment was performed as follows. After differential and electrical diagnosis, the carious cavity was mechanically worked up and shaped. Then the cavity was washed with a 3% hydrogen peroxide solution, dried with a sterile tampon, and a cotton tampon abundantly soaked in a physiological solution—based 2% preparation of the active principle was inserted therein. The walls of the cavity were then dried with a sterile cotton ball and a thin layer of the preparation paste was applied. The excess of the paste was removed from the walls, the cavity was additionally covered with artificial dentin, and after shaping the bottom thereof it was filled up.

Control examination of the treated patients revealed complete clinical recovery of all the persons examined.

Another example of the chemotherapeutic antimicrobial preparation intended for use in stomatology is a paste of the following composition (in parts by weight):

| active principle | 7 |
|---|---|
| peach kernel oil | 22 |
| artificial dentin | 71 |

The paste of the above composition was prepared ex tempera as hereinbefore described.

This paste was tested in treating acute general pulpitis of 96 teeth in 81 patients, acute partial pulpitis of 180 teeth in 132 patients, ordinary chronic pulpitis of 93 teeth in 66 patients, and hypertrophic pulpitis of 51 teeth in 42 patients.

In all said cases the treatment was performed in the following manner. The cavity in sore teeth was opened, subjected to sparing mechanical treatment, washed with a 3% hydrogen peroxide solution and dried; then into the shaped cavity a tampon was inserted, abundantly soaked in a physiological solution—based 2% active principle preparation. After removing the tampon the cavity was dried, a layer of the paste of the above composition was applied to the pulp without pressure, and the cavity was closed with artificial dentin for 2 to 3 days. After this period the cavity was opened and filled up in a conventional manner.

Recurrences in treated patients were not observed for 1.5 to 2 years.

Investigations have shown that the only contraindication for the use of chemotherapeutic preparations based on bis-(N,N-dimethyl-N-carbodecyloxymethyl-N-ethyleneammonium)-sulphide dichloride is individual intolerance.

In addition to the above-described therapeutic properties, bis-(N,N-dimethyl-N-carbodecyloxymethyl-N-ethyleneammonium)-sulphide dichloride may be used as a plant growth regulator.

The effect of the preparation was studied for 7 days under laboratory conditions on lettuce and oats plants.

The standards used in the tests were chlorocholine chloride whose structure is close to the studied chemical compound and heteroauxin phytohormone. Experiments on lettuce and oats growing in the presence of the above substances at a concentration of from 0.1 to 0.00001 wt.% were performed in Petri dishes with the use of agar medium as a substrate.

The seeds were placed into Petri dishes on solidified agar containing the test substance in the concentration indicated. The seeds germinated in a thermostat for 3 days at a temperature of from 22° to 24° C. Petri dishes with the sprouts were then placed for further growth into an exhausting hood with illumination for 4 days, whereafter the length of the roots, stalks and leaves of the sprouts was measured.

Results of measurements are given in Table 4.

TABLE 4

Effect of bis-(N,N—dimethyl-N—carbodecyloxymethyl-N—ethyleneammonium)-sulphide dichloride, chlorocholine chloride, and heteroauxine on the development of lettuce and oats sprouts

| Item | | Concentra- | Plant parts length | | | | Germination capacity | |
|---|---|---|---|---|---|---|---|---|
| | | | Lettuce | | Oats | | | |
| No. | Preparation | tion, wt. % | Root | Stalk | Root | Leaf | Lettuce | Oats |
| 1 | 2 | 3 | 4 | 5 | 6 | 7 | 8 | 9 |
| 1. | Bis-(N,N—dimethyl- | 0.1 | 2 | 0 | 6 | 55 | 0 | 87 |
| | N—carbodecyloxy- | 0.01 | 15 | 38 | 54 | 93 | 34 | 86 |
| | methyl-N—ethylene- | 0.001 | 88 | 91 | 88 | 96 | 100 | 87 |
| | ammonium)-sulphide | 0.0001 | 96 | 99 | 86 | 99 | 89 | 87 |
| | dichloride | 0.00001 | 91 | 91 | 100 | 105 | 86 | 91 |
| | Chlorocholine chloride standard | 0.01 | 101 | 99 | 94 | 96 | 94 | 98 |
| 2. | [ClCH$_2$CH$_2$N(CH$_3$)$_3$]$^\oplus$ Cl$^\ominus$ | 0.001 | 102 | 110 | 92 | 97 | 94 | 99 |
| | | 0.0001 | 104 | 98 | 102 | 94 | 98 | 91 |
| | Heteroauxine standard | 0.01 | 0 | 0 | 19 | 35 | 0 | 84 |
| 3. | 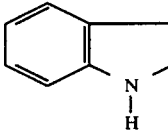 | 0.001 | 27 | 24 | 28 | 67 | 55 | 102 |
| | | 0.0001 | 88 | 92 | 88 | 92 | 81 | 100 |

As can be seen from the Table, bis-(N,N-dimethyl-N-carbodecyloxymethyl-N-ethyleneammonium)-sulphide dichloride is similar to heteroauxine phytohormone as to its inhibiting effect on plant growth. The test substance is more phytoncidal, for lettuce (dicotyledonous), whereas for oats (monocotyledonous) it more strongly inhibits the growth of roots than that of leaves. At a concentration of 0.1 wt.% it acts on dicotyledonous plants as a selective herbicide.

It must also be noted that the inhibiting action of bis-(N,N-dimethyl-N-carbodecyloxymethyl-N-ethyleneammonium)-sulphide dichloride manifests itself during 3 to 5 days after seed sowing, whereas chlorocholine chloride (conventional growth inhibitor) begins to inhibit stalk growth only after 5 to 8 days and does not inhibit root development at a concentration of 0.01 wt.%.

The toxicity of the test substance is much lower than that of chlorocholine chloride used in agriculture ($LD_{50}$ for rats is 250 mg/kg), which is a material advantage.

Test results suggest that bis-(N,N-dimethyl-N-carbodecyloxymethyl-N-ethyleneammonium)-sulphide dichloride possesses plant growth regulating properties and may be of practical interest in agriculture.

Specifically, aqueous solutions comprising from 0.0001 to 0.1 wt.% of bis-(N,N-dimethyl-N-carbodecyloxymethyl-N-ethyleneammonium,-sulphide dichloride may be used as a lodging retardant for cereals (wheat, rye, barley, oats); a stalk growth retardant for tomato and egg-plant seedings and cabbage sprouts, which is especially preferable under hothouse conditions; as a means for obtaining trunk forms of tomatoes, grape-vine, and berry- and fruit-bearing plants; as well as a peduncle growth retardant for ornamental plants such as carnation, gydrangea, freesia in case of the light day.

The present invention resides also in the provision of a method for preparing a novel substance, namely, bis-(N,N-dimethyl-N-carbodecyloxymethyl-N-ethyleneammonium)-sulphide dichloride, obtained by quaternization of bis-($\beta$-dimethylaminoethyl)-sulphide with monochloroacetic acid decyl ester along the following path:

$(CH_3)_2N-CH_2-CH_2-S-CH_2-CH_2-N(CH_3)_2$ +

$2ClCH_2COOC_{10}H_{21}$

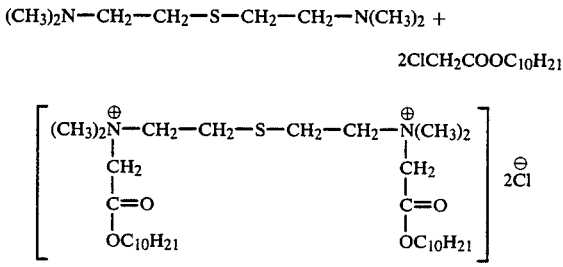

Said reagents are taken in a molar ratio of not more than 1:2.

The above reaction may be conducted directly in a mixture of bis-($\beta$-dimethylaminoethyl)-sulphide and monochloroacetic acid decyl ester.

In this case the process proceeds as follows. A mixture of the above reagents which remain liquid at room temperature gets heated as a result of exothermic reaction. The mixture is agitated to provide a high yield and prevent decomposition of the product. 1.5 to 2 hours after the beginning of the process the mixture gets heated to a temperature of about 80° C. and begins to solidify due to the crystallization of the forming product. At this moment the agitation is stopped. The temperature of the solidifying mixture rises to 95° C. due to the latent heat and as a result of heating in the further course of the reaction, and then gradually lowers to room temperature. The end product is isolated from the cooled reaction mass by conventional methods.

The reaction of quaternization of bis-($\beta$-dimethylaminoethyl)sulphide with monochloroacetic acid decyl ester is preferably conducted in a solvent (acetone) at a temperature of from 50° to 70° C. for not less than 4 hours with subsequent cooling of the reaction mass to a temperature of not over 20° C. and separation of the precipitated end product by filtration.

In this case the reaction conditions are milder, the yield of the end product is higher and the isolation thereof is simplified.

EXAMPLE 22 g of bis-($\beta$-dimethylaminoethyl)sulphide was placed into a glass reactor equipped with a stirrer, reflux condenser and a thermometer, then 63.6 g of monochloroacetic acid decyl ester was added, and the stirrer was actuated. Within 1.5 to 2 hours the reaction mass became spontaneously heated to 80° C. and began to solidify. The stirrer was then cut out. The reaction mass got crystallized. The temperature rose to 90° to 95° C. and then dropped. After the reaction mass cooled to a temperature of about 20° C., it was dissolved in 200 ml of acetone while being heated and the desired product was isolated from the solution by crystallization. 52.6 g of bis-(N,N-dimethyl-N-carbodecyloxymethyl-N-ethyleneammonium)-sulphide dichloride were obtained (65% yield), the product having the melting temperature of from 156° to 158° C. (with decomposition).

EXAMPLE

A glass reactor equipped with a stirrer, a reflux condenser and a thermometer was charged with 200 ml of acetone, 22 g of bis-($\beta$-dimethylaminoethyl) sulphide, and 63.6 g of monochloroacetic acid decyl ester. The mixture was heated under stirring to a temperature of from 50° to 70° C. and then held at this temperature for at least 4 hours. The stirrer was then cut out, and the reaction mass was cooled to a temperature of not over 20° C. The precipitated end product was filtered off from the mother liquor and purified by recrystallization from acetone. The yield of bis-(N,N-dimethyl-N-carbodecyloxymethyl-N-ethyleneammonium)-sulphide dichloride after recrystallization was 77% (62.4 g). The melting temperature was from 156° to 158° C. (with decomposition). Found, %: chlorine, 10.08; nitrogen, 4.30; sulphur, 5.18. Empirical formula is $C_{32}H_{66}Cl_2N_2O_4S$. Calculated, %: chlorine, 10.98; nitrogen, 4.34; sulphur, 4.96.

What is claimed is:

1. Bis-(N,N-dimethyl-N-carbodecyloxymethyl-N-ethyleneammonium)-sulphide dichloride of the formula

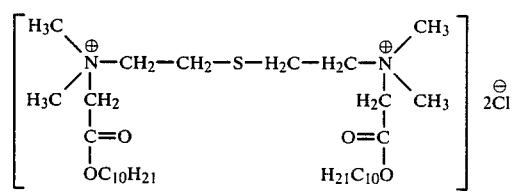

2. A chemotherapeutic antibacterial preparation comprising an effective amount of bis-(N,N-dimethyl-N-carbodecyloxymethyl-N-ethyleneammonium)sulphide dichloride active principle of the formula

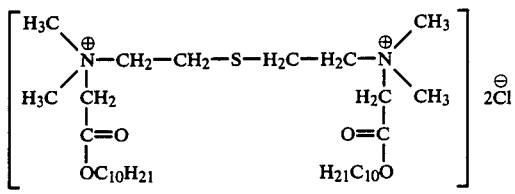

in combination with a pharmaceutical carrier.

3. A chemotherapeutic antibacterial preparation as claimed in claim 2, comprising, as a pharmaceutical carrier, physiological solution in which the concentration of the active principle ranges from 0.01 to 0.5 wt.%.

4. A chemotherapeutic antibacterial preparation as claimed in claim 3, comprising additionally from 2.5 to 3 wt.% of glycerol.

5. A chemotherapeutic antibacterial preparation as claimed in claim 2, comprising, as a pharmaceutical carrier, an ointment base in which the concentration of the active principle ranges from 0.1 to 2.0 wt.%.

6. A chemotherapeutic antibacterial preparation as claimed in claim 4, comprising a water-in-lanoline emulsion as an ointment base, said ingredients and the active principle being taken in the following ratio (in parts by weight):

| active principle | from 2 to 0.1 |
| lanoline | 80 |
| distilled water | from 18 to 19.9 |

7. A chemotherapeutic antibacterial preparation as claimed in claim 5, comprising as an ointment base, an emulsion of water in a mixture of medicinal vaseline and lanoline, said ingredients and the active principle being taken in the following ratio (in parts by weight):

| active principle | from 2 to 0.1 |
| lanoline | 40 |
| medicinal vaseline | 50 |
| distilled water | from 8 to 9.9 |

8. A chemotherapeutic antibacterial preparation as claimed in claim 2, comprising a mixture of artificial dentin and peach kernel oil as a pharmaceutical carrier, said ingredients and the active principle being taken in the following ratio (in parts by weight):

| active principle | from 5 to 7 |
| peach kernel oil | from 20 to 24 |
| artificial dentin | from 70 to 73 |

9. A plant growth regulator characterized in that it comprises bis-(N,N-dimethyl-N-carbodecyloxymethyl-N-ethyleneammonium)-sulphide dichloride as an active principle in an amount of from 0.0001 to 1.0 wt.%, water being the balance.

* * * * *